United States Patent [19]

Li

[11] 4,354,391

[45] Oct. 19, 1982

[54] SAMPLING METHOD

[76] Inventor: Chou H. Li, 379 Elm Dr., Roslyn, N.Y. 11576

[21] Appl. No.: 219,919

[22] Filed: Dec. 24, 1980

[51] Int. Cl.³ .............................................. G01N 1/04
[52] U.S. Cl. ............................. 73/863.11; 73/864.41; 164/4.1
[58] Field of Search ................ 73/863, 863.11, 863.12, 73/864.41, 864.42, 864.43; 164/4.1, 451

[56] References Cited

U.S. PATENT DOCUMENTS 766,579  8/1904  Baggaley .............................. 73/863
3,367,189  2/1968  Curry .............................. 73/863.11

FOREIGN PATENT DOCUMENTS 84716  4/1958  Denmark .............................. 164/4.1

Primary Examiner—S. Clement Swisher

[57] ABSTRACT

The invented method for sampling freeze-segregated material comprises determining a position in the segregated pattern where the elemental concentration is the same as the initial concentration, and taking a sample either at, or around the position so that the sample as a whole also has the same composition as the initial concentration.

17 Claims, 8 Drawing Figures

SAMPLING METHOD

FIELD

The invention relates to method of sampling materials and more particularly relates to method for sampling pyrometallurgically produced or melt-solidified, metal samples.

The method has special applications to precious metals having high values so that any sampling errors are financially intolerable.

PRIOR ART

Solid materials or metals in general, and precious metals in particular, have been sampled according to somewhat arbitrary methods or methods whose accuracy has not been scientifically or statistically proved. This results in inaccuracies and inconsistencies the least of which is often intolerable. The most modern or expensive instruments, the most sophisticated or time-consuming analytical techniques, and/or the best-paid analysts do not help this situation.

For example, the recommended method for sampling refined gold, according to ASTM Specification No. B562 1980-73, is to cast in a graphite mold a "pin" ⅜" or 9.5 mm or so in diameter, or to draw into a bar an elongated body after being suitably cleaned by sandpapering and acid leaching. The samples are taken by drilling once with a ¼" (6.4 mm) high-speed drill in "each of two opposite corners". The drilled holes are to be on opposite faces of the bar and also half way through the thickness of the bar, with one hole in the top face and a second hold in the bottom face. It can be shown that such a method is still too indefinite and, worse still, can yield non-representative samples.

Specifically, this ASTM method does not account for many factors including: the analytical technique or instrument used, the size of the bar, the amount and character of the impurities in the gold, the degree of stirring or mixing in the liquid during casting, the liquid diffusivity, the mold and casting temperatures, etc.

Accordingly, on object of the invention is to provide an improved method for sampling solid materials;

Another object of the invention is to provide a consistent and convenient method for sampling precious metals for a given analytical instrument or technique;

Another important object of the invention is to reduce error and uncertainty, as well as time and cost of obtaining and testing the samples;

Yet another object of the invention is to optimally vary the sampling method or position in accordance to the segregation coefficient of solute element to be analyzed, to the liquid diffusivity, to the degree of mixing in the liquid during casting, and to other casting conditions,

SUMMARY

To these ends, the present invention provides a method for sampling a pyrometallurgically treated material for the analysis of a selected chemical element which segregates during the treatment according to a fixed segregation pattern. This pattern includes a unique position or interface where the elemental concentration is the same as the initial concentration. This method comprises locating this position or interface and taking thereat a sample of the material.

BRIEF DESCRIPTION

The invention and its further objects and features will be more clearly understood from the following detailed description, taken in conjunction with the drawing in which.

DETAILED DESCRIPTION

It will be understood that specific embodiments described here are merely illustrative of the general principle of the invention, and that various modifications are feasible without departing from the spirit and scope of the invention. That is, the invented method is of general applicability for increasing the accuracy, reliability, consistency of sampling, and for reducing the cost and time of sampling. More specifically, it will be evident that the invention may be applied to various types of precious metals, other metals, nonmetals, or even combinations of metals and nonmetals. It will be apparent that materials other than those specifically mentioned or described here obviously may also be used.

In dealing with the freezing behavior of a two-component system such as a gold alloy, one can usually study the freezing segregation pattern with reference to the relevent phase diagram. The phase diagram is a temperature vs composition or concentration of the two components or elements involved. When the concentration of the impurity or solute element in the base metal or solvent is relatively low, such as less than 10 or 5% by weight, one can approximate both the liquidus and solidus of the phse diagram by two straight lines, such as are shown by the broken lines in FIGS. 1 and 2. Note that these broken lines are drawn tangentially to the solidus or liquidus at the melting point of the pure solvent. A constant segregation coefficient k is then defined as the ratio of the slope of the approximating solidus straight line to that of the approximating liquidus straight line. The solute or impurity segregation behavior due to freezing can then be expressed by the following exact equation:

$$c_s = kc_o(1-p)^{k-1}$$

where $c_s$ is the solute concentration at weight fraction p, $c_o$ is the initial (average) impurity or solute concentration, and k is the constant segregation coefficient. My invention then comprises locating the point or weight fraction $p_x$ at which the solute elemental concentration $c_s$ equals to the initial solute concentration $c_o$. This desired weight fraction, i.e., $p_x$, according to the above equation, is:

$p_x = 1 - (1/k)^{(1/k-1)}$

Table 1 gives the values of $p_x$ for various k's.

TABLE 1

| Sampling position $p_x$ vs segregation coefficient k | | | | | | |
|---|---|---|---|---|---|---|
| k = | $10^{-5}$ | $10^{-4}$ | $10^{-3}$ | $10^{-2}$ | $10^{-1}$ | 1.0 | 10.0 |
| $p_x$ = | .999990 | .9990 | .99901 | .99045 | .92257 | 0 | .22574 |

Figure 1:
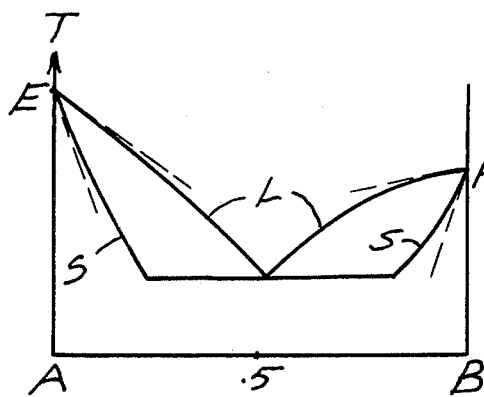
FIG. 1 shows a eutectic type phase diagram.

The segregation coefficient for a particular solute in a given solvent can be found, e.g., from the phase diagram of Hansen's Constitution of Binary Alloys, Ma-Graw-Hill, 1958. For gold alloys containing various solutes such as Cd, Mg, Mn, Pr, Sb, Si, Sn, and Zn, eutectics are formed and the relevant phase diagram is as shown in FIG. 1. For other solutes in gold solvent, the phase diagram shown in FIG. 2 should be used. These later solutes include: Cu, Pd, Pt, and Ag.

The liquidus L always lies above the solidus S in any phase diagram of two components A and B. This is, of course, because liquid solidifies on cooling and so is generally at relatively high temperature. However, the segregation coefficient k can be either greater or less than one. If the solvent or base metal (or material) is A in FIG. 2, or A or B in FIG. 1, the solidus and its approximating (broken) straight line are closer to the pure solvent (A in FIGS. 1 and 2 and B in FIG. 2), k is then less than one. That is, the solid is purer than the liquid from which it freezes out. If the solvent is the B component in FIG. 2, the solid B contains more A than the liquid it freezes out. Hence, k is greater than one.

Figure 3:
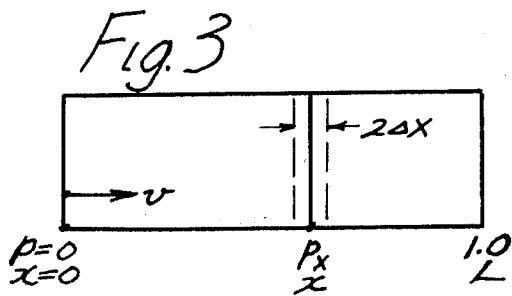
FIG. 3 shows an elongated rod frozen directionally from one end to the other.
Figure 4:
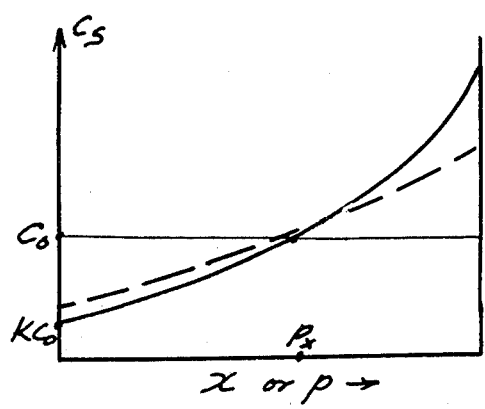
FIG. 4 shows the concentration profile of a solute element in the elongated rod frozen directionally.

If k is less than one, the impurity concentration starts at a low value, i.e., $kc_o$, and monotonically increases to pass and exceed the $c_o$ in subsequent weight fractions of the frozen material, as shown in FIG. 3. On the other hand, if k is greater than one, the solute concentration profile (i.e., $c_s$ vs p) starts at a high concentration, i.e., also $kc_o$, but monotonically decreases to pass and fall below $c_o$ in subsequent fractions forzen. Thus, no matter whether the segregation coefficient k is greater or less than one, the freezing segregation pattern is such that the solute element segregates and becomes nonuniformly distributed in the frozen material, so that a first freezing portion has a $c_s$ which is greater or less, respectively, than $c_o$; while a second or later portion has a $c_s$ which is less or greater, respectively, than $c_o$. These first and second portions join together along an interface where the solute or elemental concentration $c_s$ is substantially the same as $c_o$. My method thus comprises simply locating this interface and then taking a sample at or around this interface. In other words, my method comprises calculating the distance x or weight fraction $p_x$ in the frozen material at which the $c_s$ equals $c_o$ (FIG. 4).

When the material is frozen into an elongated rod of length L, and the freezing takes place unidirectionally along the length of the rod from one end to the other, and the rod has equal areas on all the transverse cross-sections thereof, as shown in FIG. 3, then $x = p_x L$.

When the material is frozen into a sphere of radius $r_o$ from the center outward, the interface is located at $r_x = r_o \sqrt{1-W}$, where $W = (1/k)^{(1/k-1)}$. See FIG. 5. When the material is frozen into a sphere of radius $r_o$ from the outer spherical surface toward the center of the sphere (FIG. 6), the desired $r_x = r_o \sqrt{W}$. For materials frozen into cylindrical bodies of radius $r_o$ along directions perpendicular to the cylindrical axis, either from the cylindrical surface inward or from the cylindrical axis outward, $r_x = r_o \sqrt{W}$ (FIG. 6) or $= r_o \sqrt{1-W}$ (FIG. 5), respectively.

Tables 2 and 3 give the sampling positions $p_x$ in various Au and Ag alloys.

TABLE 2

| Sampling position in various gold alloys | | | | | | | | | |
|---|---|---|---|---|---|---|---|---|---|
| Solute | Cu | Cd | Fe | Ga | Hg | In | Mg | Mn | Ni |
| k | .523 | .573 | .259 | .640 | .200 | .365 | .350 | .140 | .329 |
| $p_x$ | .743 | .729 | .838 | .710 | .866 | .796 | .801 | .899 | .809 |
| $N_r$ | 5 | 4 | 10 | 3 | 11 | 7 | 8 | 12 | 9 |
| Solute | Sb | Sn | Pd | Pt | Zn | | | | |
| k | .096 | .139 | 2.170 | 1.825 | .489 | | | | |
| $p_x$ | .925 | .899 | .484 | .518 | .753 | | | | |
| $N_r$ | 14 | 13 | 1 | 2 | 6 | | | | |

TABLE 3

| Sampling position in various silver alloys | | | | | | | | |
|---|---|---|---|---|---|---|---|---|
| Solute | Oxygen | Al | Au | Be | Cd | Cu | Ge | Hg |
| k | .0188 | .388 | 1.081 | .060 | .841 | .412 | .215 | .538 |
| $p_x$ | .983 | .787 | .618 | .950 | .663 | .778 | .860 | .739 |
| $N_r$ | 16 | 8 | 3 | 15 | 4 | 9 | 12 | 6 |
| Solute | In | Li | Mg | Pb | Pd | Pt | Sn | Zn |
| k | .598 | .102 | .150 | .270 | 4.545 | 7.692 | .418 | .298 |
| $p_x$ | .722 | .921 | .892 | .834 | .348 | .263 | .777 | .822 |
| $N_r$ | 5 | 14 | 13 | 11 | 2 | 1 | 7 | 10 | where $N_r$ is the ranking number, or the order of sampling the various solute elements along the length of the frozen rod shown in FIG. 3.

The various desired sampling positions $r_x$ can be obtained from $p_x$ by noting that $W = 1 - p_x$.

When a number of segregating elements are present together in a freezing alloy, each element has a different segregation pattern according to its unique segregation coefficient $k_i$. The above linear freezing equation shows that for all the $k_i$'s less than one, the sampling positions $x_i$'s should be located such that they (or $p_i$'s) increase with the ranking number in the above tables (Tables 2 and 3) or with decreasing values of $k_i$'s. The opposite holds, as to the values of $k_i$'s, if they are over one.

Figure 6:
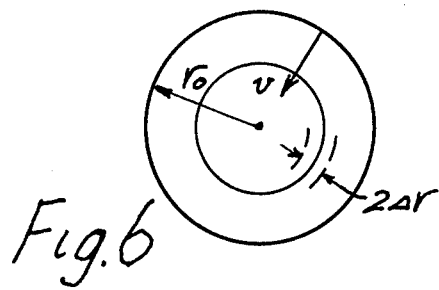
FIG. 6 shows a sphere or cylinder frozen from the spherical or cylindrical surface inward, toward the center of the sphere or the cylindrical axis, respectively.
Figure 5:
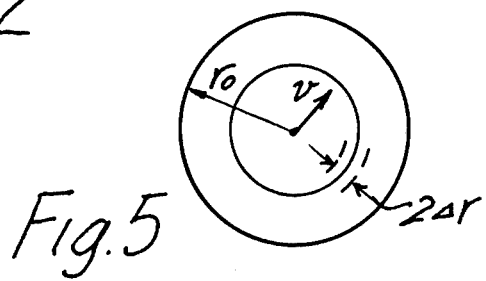
FIG. 5 shows a spherical or cylindrical body frozen from the center of the sphere or the cylindrical axis outward, respectively.

If the maximum error in $c_s$ in any part of the sample is to be less than $\Delta c_s^m$, then $\Delta c_s^m \geq \Delta c_s = (dc_s/dp)\Delta p = -k(k-1)c_o(1-p)^{k-2}\Delta p = -Q\Delta p$, where $Q = -k(k-1)c_o(1-p)^{k-2}$. For the directionally frozen rod (FIG. 3), the maximum error in x from the exact interface should then be $\Delta x^m = L\Delta p = (L/Q)\Delta c_s^m$. For the non-flat solid-liquid fronts such as are shown in FIG. 5 or 6, the maximum error in radius r from the exact (equal-concentration) interface is: $\Delta r^m = (r_o/Q \ W)\Delta c_s^m$ or $= (r_o/Q (1-W))\Delta c_s^m$, respectively.

Burton et al. in Transistor Technology, D. van Nostrand, 1958 showed that when the freezing velocity, or the rate of growth of the freezing material, v, exceeds values of about 0.001 cm/sec, one should calculate the weight fraction $p_x$ according to the same linear freezing equation given above, but with an "effective segregation coefficient $k_e$" replacing k, as follows:

$$k_e = \frac{k}{k + (1-k)\exp(-hv/D)}$$

where h is the thickness of the liquid diffusion layer in front of the freezing solid and varies from 0.001 to 0.1 cm, while D is the liquid diffusivity and varies from 0.00001 to 0.0001 cm²/sec.

Figure 2:
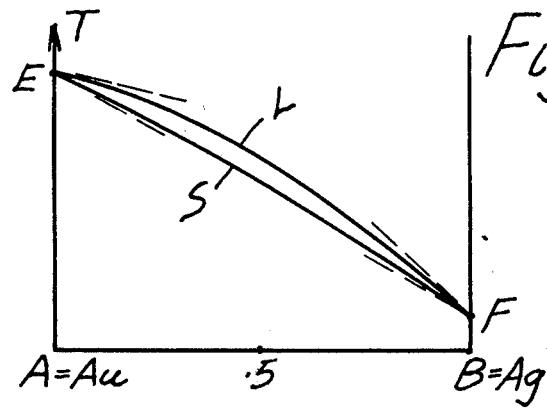
FIG. 2 shows the Au-Ag phase diagram.

As noted earlier, gold and silver have a phase diagram as shown in FIG. 2, with gold melting at 1,063° C. and silver 960.5° C. (Points E and F, respectively). One can then consider any gold-silver alloy as either a gold alloy containing solute silver with a segregation coefficient k of less than one, or a silver alloy containing gold with k of greater than one. Apparently, the segregation coefficient k is not constant. Strictly speaking and particularly when the initial concentration $c_o$ is higher than the values indicated above, the above linear freezing equation cannot be used for maximum accuracy. One can then use nonlinear freezing equations already developed or use numerical techniques together with the following, basic freezing equation:

$$\frac{dp}{1-p} = -d \ln (1-p) = \frac{L'(T)}{L(T) - S(T)} dT$$

where $L(T)$ and $S(T)$ are function of the melt temperature for the liquidus and solidus, respectively; and $L'(T)$ is the first derivative of $L(T)$ with respect to melt temperature T. The discrepancy between calculated values of p or $p_x$ obtained with the linear freezing equation and those obtained with non-constant k can be substantial, particularly when $c_o$ is large.

While the above methods give much more consistent results than the ASTM rather indefinite method, these methods still do not account for special situations such as intentional or unintentional, post-freezing heat treatments. These treatments flatten the concentration profile (See the broken profile in FIG. 4). Such deviations can be account for by additional computations taking into account heat and mass transfers, or by actual experiments, to achieve the ultimate in accuracy in the computations of $p_x$. The experiments, e.g., comprise determining the actual concentration profile ($c_s$ vs p) in the real-size bullion or ingot cast in the regular manner, with or without the post-freezing heat treatments, and then measuring the necessary adjustments in $p_x$, x, or $r_x$.

Figure 7:
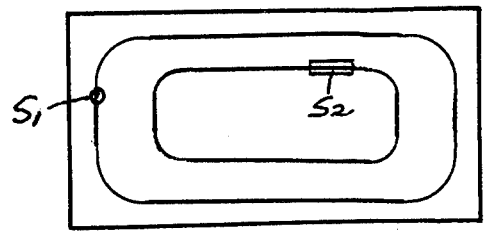
FIGS. 7 and 8 show the top view and side view, respectively, of a frozen gold bullion, with some properly located drilling positions for sampling.
Figure 8:
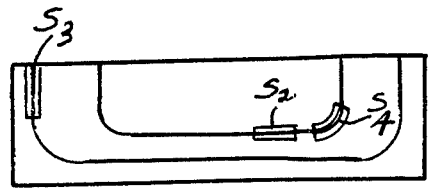
Figure 1:
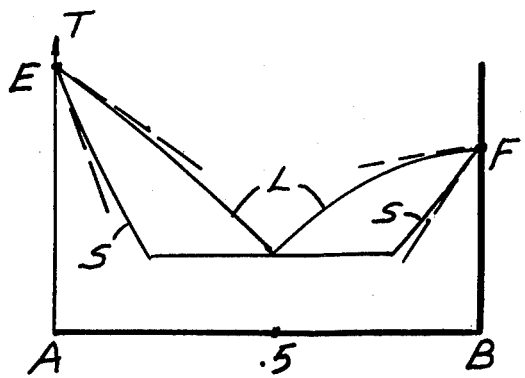
Figure 6:
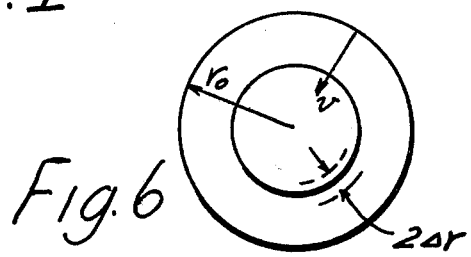
Figure 2:
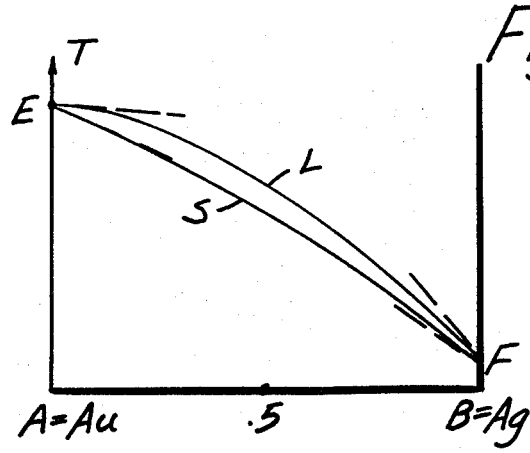
Figure 5:
Figure 3:
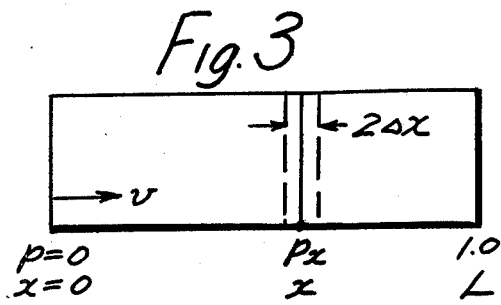
Figure 7:
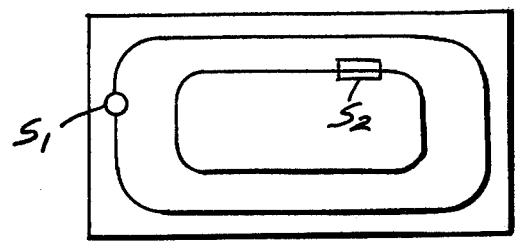
Figure 4:
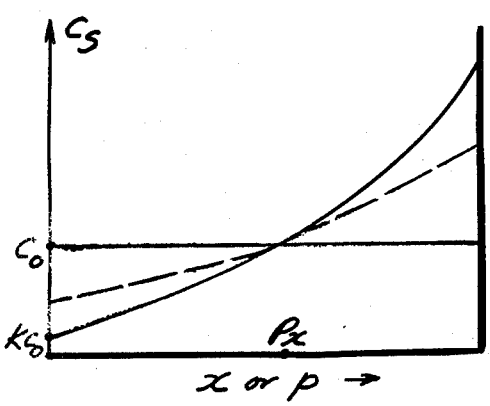
Figure 8:
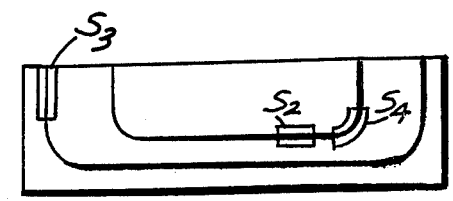

FIGS. 5 and 6 show, respectively, spheres or cylinders freezing from the center outward or from the outside surface inward at velocity v. The location of the desired sampling position (or the interface) is shown, together with the maximum error in locating distance $r_x^m$. FIGS. 7 and 8 show the top view and side view, respectively, of a frozen gold bullion or ingot. The freezing contours are also indicated together with desirable sampling positions for Auger or microprobe spot $S_1$, microanalysis of a larger sample size at position $S_2$, drill sample at position $S_3$, flat sample at $S_4$, and nonflat sample at $S_5$. The last three samples may be for wet or fire assay, or even for x-ray analysis. Thus, the collected sample material may be analyzed by a variety of designated analytical instruments including microprobe, Auger, x-ray (due to fixed relation between composition and lattice constants), wet analysis, microanalysis, fire assay, and the like. Each of these instruments requires a sample of fixed shape and size and has a fixed spatial (lateral and vertical) examination spot size, shape, and resolution. These characteristics should be kept in mind together with the shape, size, and freezing direction and velocity of the sample material, so that the sample material as a whole and as examined by the particular, designated instrument will have an average element concentration $\bar{c}_o$ which is substantially the same as the average initial elemental concentration $c_o$. In this way, the sample is truly representative.

The invention is not to be construed as limited to the particular forms disclosed herein, since these are to be regarded as illustrative rather restrictive. Various combinations, equivalent substitutions, or other modifications of the preferred embodiments described herein are obviously possible in light of the description, without departing from the spirit and scope of the invention. Accordingly, the invention is to be limited only as indicated by the scope of the following claims.

I claim:

1. A method for sampling a pyrometallurgically treated material for the analysis by a designated analytical instrument of a selected chemical element having an average initial elemental concentration $c_o$ in the material before the treatment, said treatment causing the element to segregate and to become nonuniformly distributed in the material according to a fixed segregation pattern so that in a first portion of the material the elemental concentration is above $c_o$ while in a second portion of the material the elemental concentration is below $c_o$, the first and second portions joining together along an interface where the elemental concentration substantially equals $c_o$, comprising:
   locating the interface; and
   taking a sample of the treated material in a specified shape and size and oriented and spaced relative to the interface so that the sample as a whole has substantially the same elemental concentration as $c_o$.

2. The method as in claim 1 wherein the pyrometallurgical treatment comprises a melt freezing treatment and the segregation pattern is a melt-segregation pattern of the material in molten form and freezing out and segregating the chemical element according to collected freezing segregation data of the material and the element and the locating step comprises calculating the distance in the frozen material at which the segregated elemental concentration equals $c_o$.

3. The method as in claim 2 wherein the freezing segregation data comprise a phase diagram of the material and the element and the locating step comprises calculating the distance by use of the phase diagram.

4. The method as in claim 3 including actually determining the concentration profile in the treated material and applying the necessary corrections to the calculated distance.

5. The method as in claim 3 wherein the frozen material is further subjected to post-freezing heat treatment causing significant modification of the segregation pattern and including adjusting the calculated distance according to the modification caused by the post-freezing heat treatment.

6. The method as in claim 3 wherein the taking step comprises collecting a sample substantially at the interface.

7. The method as in claim 6 wherein the interface is substantially planar and the taking step comprises collecting a flat sample substantially at and parallel to the interface.

8. The method as in claim 6 wherein the interface is nonplanar and the taking step comprises collecting a nonplanar sample generally centered at and locally substantially parallel to the interface.

9. The method as in claim 3 wherein the phase diagram has a substantially constant segregation coefficient k and the calculating step comprises computing the weight fraction frozen $p_x$ according to: $p_x = 1 - W = 1 - (1/k)^{(1/(k-1))}$, where $W = (1/k)^{(1/(k-1))}$.

10. The method as in claim 9 wherein the material is frozen into an elongated rod of length L, the freezing taking place directionally along the length from one end to the other and the rod having nearly equal areas on the transverse cross-sections thereof, and the calculating step comprises computing the distance x in the frozen rod material from the one end according to: $x = p_x L$.

11. The method as in claim 9 wherein the material is frozen into a sphere of radius $r_o$ from the outer spherical surface toward the center of the sphere and the calculating step comprises computing the radius $r_x$ according to: $r_x = r_o \sqrt{W}$.

12. The method as in claim 9 wherein the material is frozen into a sphere of radius $r_o$ from the center outward and the calculating step comprises computing the radius $r_x$ according to: $r_x = r_o \sqrt{1-W}$.

13. The method as in claim 9 wherein the material is frozen to a cylinder of radius $r_o$ along directions perpendicular to the cylindrical axis and the calculating step comprises computing the radius $r_x$ according to: $r_x = r_o Q$, where Q is the square root of a linear function of W.

14. The method as in claim 9 wherein the material is frozen at a velocity in excess of 0.001 cm/sec and the calculating step comprises computing the weight fraction frozen $p_x$ according to the equation given in claim 9 but with an effective segregation $k_e$ replacing k where: $k_e = k/(k + (1-k) \exp(-vh/D))$ and h is the thickness of the liquid diffusion layer in front of the solid-liquid interface and varies from about 0.001 to 0.1 cm while D is the liquid diffusivity lying between 0.00001 to 0.001 cm$^2$/sec.

15. The method as in claim 9 wherein the maximum error in elemental concentration at any point in the sample is to be less than $\Delta c_s^m$, and including limiting the maximum deviation in the computed distance x from the interface $\Delta x$ such that $\Delta x$ is less than $\Delta c_s^m L / (k c_o (k-1)(1-p)^{k-2})$ when the material is frozen into a rod of uniform cross-section and length L.

16. The method as in claim 9 wherein the material is frozen out unidirectionally and contains a plurality of segregating elements having substantially constant segregation coefficients $k_i$'s, and the locating and taking steps comprise locating the respective interfaces for the elements and taking multiple samples in the order of ranking numbers $N_r$ given in Tables 2 and 3 of the specification.

17. The method as in claim 3 wherein the phase diagram has a non-constant segregation coefficient which varies with the melt temperature and composition.

* * * * *